(12) United States Patent
Ekkundi et al.

(10) Patent No.: US 6,620,960 B2
(45) Date of Patent: Sep. 16, 2003

(54) PROCESS FOR THE PREPARATION OF SUBSTITUTED PHENYLACETONITRILES

(75) Inventors: Vadiraj S. Ekkundi, Mumbai (IN); Vilas N. Mumbaikar, Mumbai (IN); Niranjan Paingankar, Mumbai (IN); Paul Adriaan Van Der Schaaf, Allschwil (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/130,010
(22) PCT Filed: Aug. 21, 2001
(86) PCT No.: PCT/EP01/09665
§ 371 (c)(1), (2), (4) Date: Oct. 1, 2002
(87) PCT Pub. No.: WO02/18325
PCT Pub. Date: Mar. 7, 2002

(65) Prior Publication Data
US 2003/0139623 A1 Jul. 24, 2003

(30) Foreign Application Priority Data
Aug. 30, 2000 (IN) .................................. 705/MAS/2000

(51) Int. Cl.$^7$ .................... C07C 253/30; C07C 255/00
(52) U.S. Cl. ..................................... 558/371; 564/164
(58) Field of Search ........................ 558/371; 564/164

(56) References Cited

U.S. PATENT DOCUMENTS 5,043,466 A * 8/1991 Shepard ................ 558/371
6,504,044 B2 * 1/2003 Chavan et al. .......... 558/371

* cited by examiner

Primary Examiner—Cecilia Tsang
Assistant Examiner—Ebenezer Sackey
(74) Attorney, Agent, or Firm—Kevin T. Mansfield

(57) ABSTRACT

Disclosed is a process for the preparation of a compound of the formula (1) wherein $R_1$ is unsubstituted or substituted sing reacting a compound of the formula (2) with a compound of the formula (3) in the presence of an aqueous base ransfer catalyst.

14 Claims, No Drawings

PROCESS FOR THE PREPARATION OF SUBSTITUTED PHENYLACETONITRILES

This application is a 371 of PCT/EP01/09665 filed Aug. 21, 2001.

The present invention is directed to a process for the preparation of substituted phenylacetonitriles which is carried out by the reaction of alkoxyphenylacetonitriles with cyclohexanone in the presence of an aqueous base and a phase transfer catalyst.

Substituted phenylacetonitriles of formula (1) are known for being particularly useful as synthesis intermediates for preparing pharmaceutical active substances which are central nervous system antidepressants. An important substance is Venlafaxine (see Merck Index Twelfth Edition 1996, No. 10079). The preparation of this compound is described in U.S. Pat. No. 4,535,186.

According to U.S. Pat. No. 4,535,186, Example 1, intermediates of formula (1) are prepared by the reaction of p-methoxyphenylacetonitrile and cyclohexanone in the presence of n-butyl lithium and an organic solvent, like tetrahydrofuran and cyclohexane. The overall yield according to this process is low and does not exceed 50%. Furthermore, the use of n-butyl lithium and organic solvents provides environmental as well as economical drawbacks and results in a process wherein the reaction conditions have to be carefully controlled.

It is the object of the present invention to provide a process for the preparation of substituted phenylacetonitriles with improved yield, which also meets environmental as well as economical demands and wherein the reaction conditions can easily be controlled.

The present invention relates to a process for the preparation of a compound of formula

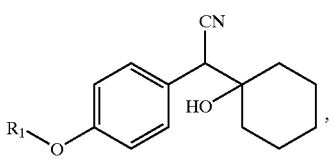

(1)

wherein $R_1$ is unsubstituted or substituted alkyl, comprising reacting a compound of formula

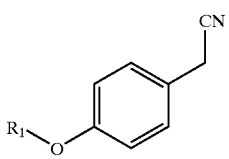

(2)

with a compound of formula

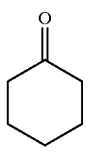

(3)

in the presence of an aqueous base and a phase transfer catalyst.

Preferably, $R_1$ is $C_1$–$C_{10}$alkyl, especially $C_1$–$C_4$alkyl; an example for a substituent of the alkyl radical $R_1$ is phenyl.

Examples for $R_1$ are methyl, ethyl, n- or i-propyl, n-, i-, sec- or tert-butyl, and benzyl. Most preferably $R_1$ is methyl.

The amount of the compound of formula (3) used is preferably 0.9 to 1.8, preferably about 1 to 1.6 molar equivalents relative to the molar amount of the compound of formula (2).

The aqueous base is preferably an aqueous solution of an alkali hydroxide, especially an aqueous solution of sodium hydroxide or potassium hydroxide, most preferably sodium hydroxide.

The amount of the base used is preferably 0.05 to 4, preferably 0.1 to 2 and most preferably 0.25 to 1.5 molar equivalents relative to the molar amount of the compound of formula (2).

An aqueous solution of the base usually comprises 1 to 70%, preferably 1 to 60% by weight of the base, based on the total of the weight of water and the base. A minimum amount of the base of 3%, especially 5% by weight is preferred. The maximum amount of the base is preferably 50%, most preferably 25%.

Examples of phase transfer catalysts are described in WO-A-97/20810, page 6, line 13 to page 7, line 5 which is hereby incorporated by reference.

Preferred as phase transfer catalysts are quaternary ammonium salts, quaternary phosphonium salts or crown ethers.

Most preferably, the phase transfer catalyst is a compound of formula $$N(R_2)_4{}^+Hal^- \quad (4a)$$

or $$P(R_3)_4{}^+Hal^- \quad (4b),$$

wherein each of $R_2$ and $R_3$ independently from the other substituents $R_2$ and $R_3$ is phenyl or alkyl which is unsubstituted or substituted by phenyl, and $Hal^-$ is a halide.

$R_2$ and $R_3$ are preferably $C_1$–$C_{16}$alkyl, benzyl or phenyl, especially $C_1$–$C_4$alkyl, benzyl or phenyl. Most preferably, $R_2$ and $R_3$ are $C_1$–$C_4$alkyl or benzyl, especially $C_1$–$C_4$alkyl. Highly preferred for $R_2$ and $R_3$ is $C_3$–$C_4$alkyl, especially butyl.

Examples for $Hal^-$ are fluoride, chloride, bromide and iodide. Preferably $Hal^-$ is fluoride, chloride or bromide, most preferably chloride or bromide. Highly preferred is bromide.

Phase transfer catalysts of formula (4a) are preferred. Highly preferred phase transfer catalysts are tetrabutylammonium chloride or bromide, especially tetrabutylammonium bromide.

It is of course also possible to use mixtures of phase transfer catalysts.

The amount of the phase transfer catalyst used is as a rule in the range of from 0.0001 to 0.1, especially 0.0005 to 0.05 molar equivalents relative to the molar amount of the compound of formula (2). A minimum amount of the phase transfer catalyst of 0.001 is preferred.

The reaction of compound of formula (2) with compound of formula (3) is carried out at a temperature of 0 to 60° C., especially 0 to 40° C. It is preferred to carry out the reaction at a temperature of 15 to 35° C., especially at room temperature.

As to the reaction it is not necessary to add any organic solvents. This means, that the reaction usually is carried out by addition of the reactants, aqueous solution of the base and phase transfer catalyst.

According to a preferred embodiment the reaction of compound of formula (2) with compound of formula (3) is carried out in the presence of an aqueous solution of sodium or potassium hydroxide, especially sodium hydroxide, and in the presence of a phase transfer catalyst of formula (4a), wherein $R_2$ is $C_1$–$C_4$alkyl, especially butyl, and Hal⁻ is chloride or bromide.

After the reaction is completed the desired product can be separated, for example by filtration. If desired the product can be washed and subsequently be dried.

Furthermore, the present invention is directed to a process for the preparation of a compound of formula

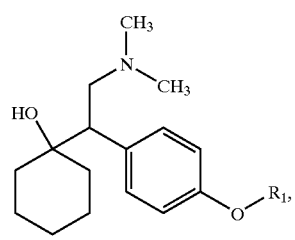

(5)

wherein $R_1$ is unsubstituted or substituted alkyl, comprising reacting a compound of formula

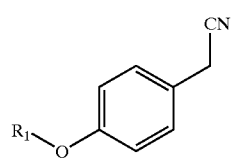

(2)

with a compound of formula

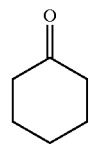

(3)

in the presence of an aqueous base and a phase transfer catalyst to give the compound of formula

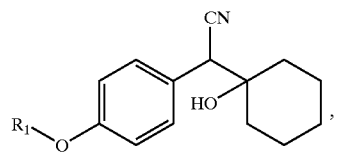

(1)

wherein $R_1$ is as defined above, and converting the compound of formula (1) to the compound of formula (5).

As given above, the compounds of formula (1) are suitable intermediates for the preparation of Venlafaxine which is represented by the formula (5).

As to $R_1$ the above definitions and preferences apply. Most preferably, $R_1$ is methyl.

The conversion of the compound of formula (1) to the compound of formula (5) can be carried out according to known processes. Such a conversion and the reaction conditions to be used are described in U.S. Pat. No. 4,535,186 (see especially Examples 2 and 3).

In general, a method for such a conversion comprises the following steps:

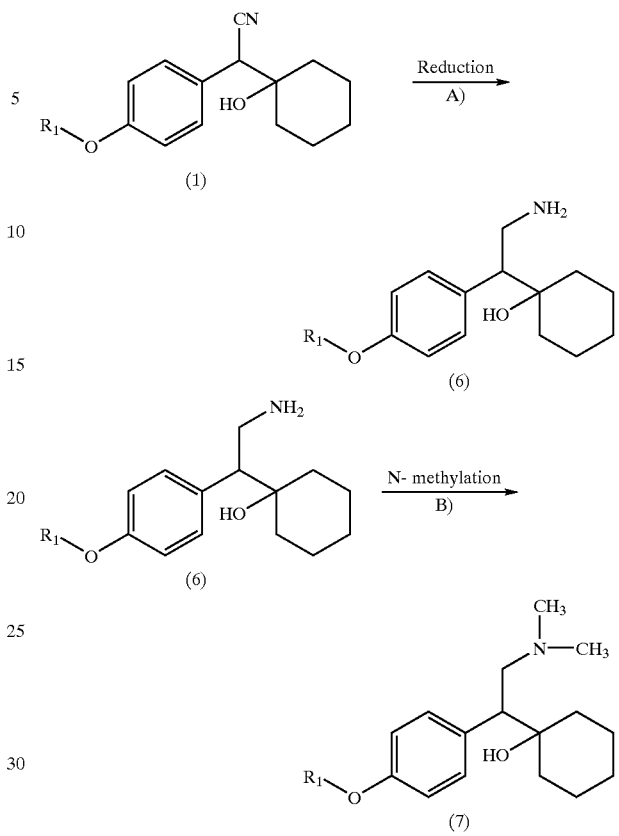

Steps A) can be carried out by catalytic hydrogenation (for example rhodium on alumina).

Steps B) can be carried out by reaction of the compound of formula (6) with formaldehyde, formic acid in a large excess of water.

According to the present invention the intermediates of formula (1) can be obtained in high yields. The use of organic solvents and also of expensive bases can be dispensed with. Furthermore, the reaction can be easily controlled.

The following examples illustrate the invention:

EXAMPLES 1 to 8

4-methoxyphenyl)acetonitrile and cyclohexanone are mixed and warmed/cooled to the desired temperature given in the following table. The phase transfer catalyst (PTC) and the aqueous base solution are added under vigorous stirring. The resulting reaction mixture is stirred for the time given in the following table, and subsequently filtered. The solid product is washed with water and dried in vacuum.

The reaction conditions are given in the following table. The equivalents given in the table are molar equivalents relative to the molar amount of (4-methoxyphenyl) acetonitrile

TABLE

Experimental conditions

| Ex. | Aqueous base solution | equivalents of the base | PTC | equivalents of cyclohexanone | Time | Temp. (° C.) | Yield |
|---|---|---|---|---|---|---|---|
| 1 | 10% NaOH | 0.46 | TBAB 0.2 mol % | 1.3 | 8 h | 27 | 90% |
| 2 | 10% NaOH | 0.46 | TBAB 0.2 mol % | 1.35 | 8 h | 27 | 90% |
| 3 | 10% NaOH | 1 | TBAB 0.2 mol % | 1.4 | 2 h | 27 | 95% |
| 4 | 10% NaOH | 0.46 | TBAB 0.1 mol % | 1.1 | 2 h | 27 | 92% |
| 5 | 10% NaOH | 0.46 | TBAB 0.2 mol % | 1.4 | 6 h | 18 | 91% |
| 6 | 10% NaOH | 0.46 | TBAB 0.2 mol % | 1.35 | 6 h | 18 | 91% |
| 7 | 10% KOH | 0.46 | TBAB 0.2 mol % | 1.4 | 6 h | 18 | 91% |
| 8 | 10% NaOH | 0.46 | TBACI 0.2 mol % | 1.4 | 6 h | 18 | 95% |

TBAB = tetrabutylammonium bromide
TBACI = tetrabutylammonium chloride

What is claimed is:

1. A process for the preparation of a compound of formula

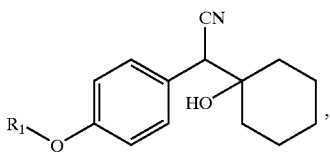
(1)

wherein $R_1$ is unsubstituted or substituted alkyl, comprising reacting a compound of formula

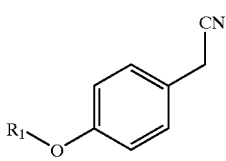
(2)

with a compound of formula

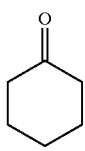
(3)

in the presence of an aqueous base and a phase transfer catalyst.

2. A process according to claim 1, wherein $R_1$ is $C_1$–$C_4$alkyl which is unsubstituted or substituted by phenyl.

3. A process according to claim 1, wherein $R_1$ is methyl.

4. A process according to claim 1 wherein the aqueous base is an aqueous solution of an alkali hydroxide.

5. A process according to claim 1 wherein the aqueous base is an aqueous solution of sodium hydroxide or potassium hydroxide.

6. A process according to claim 1, wherein the phase transfer catalyst is a quaternary ammonium salt, a quaternary phosphonium salt or a crown ether.

7. A process according to claim 1, wherein the phase transfer catalyst is a compound of formula $$N(R_2)_4{}^+Hal^- \qquad (4a)$$

or $$P(R_3)_4{}^+Hal^- \qquad (4b),$$

wherein each of $R_2$ and $R_3$ independently from the other substituents $R_2$ and $R_3$ is phenyl or alkyl which is unsubstituted or substituted by phenyl, and $Hal^-$ is a halide.

8. A process according to claim 7, wherein $R_2$ and $R_3$ are $C_1$–$C_{16}$alkyl, benzyl or phenyl.

9. A process according to claim 7, wherein the phase transfer catalyst is a compound of formula (4a) and $R_2$ is $C_1$–$C_4$alkyl.

10. A process according to claim 7, wherein $Hal^-$ is fluoride, chloride or bromide.

11. A process according to claim 1, wherein the reaction of compound of formula (2) with compound of formula (3) is carried out at a temperature of 0 to 60° C.

12. A process according to claim 1, wherein the reaction of compound of formula (2) with compound of formula (3) is carried out in the presence of an aqueous solution of sodium or potassium hydroxide and in the presence of a phase transfer catalyst of formula $$N(R_2)_4{}^+Hal^- \qquad (4a)$$

wherein $R_2$ is $C_1$–$C_4$alkyl and $Hal^-$ is chloride or bromide.

13. A process for the preparation of a compound of formula

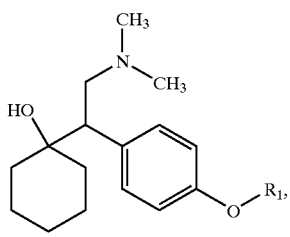

(5)

wherein $R_1$ is unsubstituted or substituted alkyl, comprising reacting a compound of formula

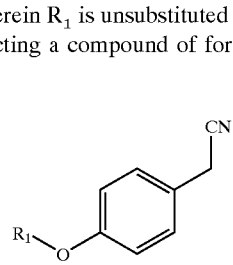

(2)

with a compound of formula

(3)

in the presence of an aqueous base and a phase transfer catalyst to give the compound of formula (1)

wherein $R_1$ is as defined above, and converting the compound of formula (1) to the compound of formula (5).

14. A process according to claim 13 wherein $R_1$ is methyl.

* * * * *